(12) United States Patent
Dodd et al.

(10) Patent No.: US 9,499,784 B2
(45) Date of Patent: Nov. 22, 2016

(54) PROCESS FOR PRODUCTION OF MICROALGAE, CYANOBACTERIA AND METABOLITES THEREOF INCLUDING LIPIDS AND CARBOHYDRATES

(75) Inventors: John Dodd, Kent (GB); Blahsolov Marsalek, Brno (CZ); Miroslav Vosatka, Pruhonice (CZ); Nazir Bashir, Kent (GB)

(73) Assignee: Algaecytes Limited, Kent (GB)

( * ) Notice: Subject to any disclaimer, the term of this patent is extended or adjusted under 35 U.S.C. 154(b) by 0 days.

(21) Appl. No.: 13/981,999

(22) PCT Filed: Jan. 30, 2012

(86) PCT No.: PCT/GB2012/050194
§ 371 (c)(1),
(2), (4) Date: Oct. 31, 2013

(87) PCT Pub. No.: WO2012/101459
PCT Pub. Date: Aug. 2, 2012

(65) Prior Publication Data
US 2014/0051131 A1 Feb. 20, 2014

(30) Foreign Application Priority Data

Jan. 28, 2011 (GB) .................................. 1101487.5
Jan. 28, 2011 (GB) .................................. 1101489.1

(51) Int. Cl.
| | |
|---|---|
| C12N 1/12 | (2006.01) |
| C12N 13/00 | (2006.01) |
| C12P 19/04 | (2006.01) |
| C05F 11/00 | (2006.01) |
| C05F 17/00 | (2006.01) |
| C12N 1/36 | (2006.01) |
| C12P 7/64 | (2006.01) |
| C12R 1/89 | (2006.01) |
| C12M 1/00 | (2006.01) |
| C12M 1/34 | (2006.01) |

(52) U.S. Cl.
CPC ................ *C12N 1/12* (2013.01); *C05F 11/00* (2013.01); *C05F 17/0036* (2013.01); *C05F 17/0081* (2013.01); *C12M 21/02* (2013.01); *C12M 41/06* (2013.01); *C12M 41/26* (2013.01); *C12N 1/36* (2013.01); *C12N 13/00* (2013.01); *C12P 7/64* (2013.01); *C12P 7/6427* (2013.01); *C12P 19/04* (2013.01); *C12R 1/89* (2013.01); *Y02P 20/145* (2015.11); *Y02W 30/43* (2015.05)

(58) Field of Classification Search
CPC .......... C12N 1/12; C12N 13/00; C12M 21/02; C12R 1/89; C12P 10/04
USPC ..................... 455/101, 257.1, 245
See application file for complete search history.

(56) References Cited

U.S. PATENT DOCUMENTS

2009/0047722 A1  2/2009  Wilkerson et al.

FOREIGN PATENT DOCUMENTS

| | | |
|---|---|---|
| JP | 07-075556 | 3/1995 |
| JP | 2006-503556 | 2/2006 |
| WO | 2004009826 | 1/2004 |
| WO | 2006085144 | 8/2006 |
| WO | 2009142765 | 11/2009 |
| WO | 2010009284 | 1/2010 |
| WO | 2011035042 A2 | 3/2011 |

OTHER PUBLICATIONS

Katsuda et al. Astaxanthin Production by Haematococcus Pluvialis Under Illuminiton With LEDS; Enzyme and Microbial Technology, vol. 35, No. 1 (2004) pp. 81-86.*
Kang et al. Productive Encystment of Haematococcus Pluvialis by Controlling a Specific Irradiation Rate in a Photoautotrophic Induction System for Astaxanthin Production; Journal of Industrial and Engineering Chemistry, vol. 12, No. 5 (2006) pp. 745-748.*
Imamoglu et al. Influences of Different Stress Media and High Light Intensities on Accumulation of Astaxanthin in the Green Alga *Haematococcus pluvialis*; New Biotechnology, vol. 26, No. 3/4 (2009) pp. 199-204.*
Zhekisheva et al. Accumulation of Oleic Acid in Haematococcus Pluvialis (Chlorophyceae) Under Nitrogen Starvation or High Light is Correlated With That of Astaxanthin Esters; Journal of Phycology, vol. 38 (2002) pp. 325-331.*
Dayananda et al. Autotrophic Cultivation of Botryococcus Braunii for the Production of Hydrocarbons and Exopolysaccharides in Various Media; Biomass and Bioenergy, vol. 31 (2007) pp. 87-93.*
Bermudez et al. Exopolysaccharide, Pigment, and Protein Production by the Marine *Microalga chroomonas* sp. in Semicontinuous Cultures; Worl Journal of Microbiology and Biotechnology, vol. 20 (2004) pp. 179-183.*
Anonymous. Algaenase Taxonomy Browser, Phylum: Chlorophyta (2015), pp. 1-3; downloaded from http://www.algaebase.org/browse/taxonomy/?id=97241&-session=abv4:97CFFA3D1896b35D54mm81ED680A on Oct. 7, 2015.*

(Continued)

*Primary Examiner* — Scott Long
*Assistant Examiner* — Paul Martin
(74) *Attorney, Agent, or Firm* — Andrus Intellectual Property Law, LLP

(57) ABSTRACT

The present invention relates to processes for the production of microalgae, cyanobacteria and/or metabolites thereof. Described herein is a process involving, the use of a stimulus applied to a microalgal or cyanobacterial culture to enhance the production of one or more metabolites. Also described herein, is a process for the production of microalgae and/or cyanobacteria comprising an adaptation stage wherein an algal/cyanobacterial culture is grown on a process water feedstock and/or under light emitting diodes (LEDs) emitting light within the spectrum of light wavelengths between around 400 nm and 700 nm, and a production phase, wherein the microalgae or cyanobacteria are grown on the same process water feedstock and/or under the same light conditions used in the adaptation stage. The invention also relates to specific microalgal strains.

8 Claims, 9 Drawing Sheets

(56) References Cited

OTHER PUBLICATIONS

Anonymous. Algaebase Taxonomy Broswer, Family Pleurochloridaceae (2015) pp. 1-3; downloaded from http://wwwalgaebase.org/browse/taxonomy/?id=4898 on Oct. 7, 2015.*

Guang et al., "Effects of Temperature, Light and pH on Photosynthesis, and of Light-dark Cycle on Growth Rate and biomass of Scrippsiella trochoidea and Alexandrium tamarense", Journal of Wuhan Botanical Research, 2004, 22 (2):129-135.

Wang et al., "Effect of pH growth and lipid content of Chlorella vulgaris cultured in biogas slurry", Chin J Biotech, Aug. 25, 2010, 26(8):1074-1079.

Yuxiang et al., "Enhanced production of volatile fatty acids form waste algae in Taihu Lake under alkaline condition", Chinese Journal of Environmental Engineering, Jan. 2010, 4(1):209.

Search Report for GB1101489.1 dated May 27, 2011.

Search Report for GB1101487.5 dated May 23, 2011.

Alcoverro, "Production of Mucilage by the Adriatic Epipelic Diatom *Cylindrotheca closterium* (Bacillariophyceae) Under Nutrient Limitation", Journal of Phycology, 2000, 36:1087-1095.

Bitton et al., "Novel Biomimetic Adhesives Based on Algae Glue", Macromolecular Bioscience, 2008, 8:393-400.

Braun, "Re-Use and Fixation of CO2 in Chemistry, Algal Biomass and Fuel Substitutions in the Traffic Sector", Energy Conversion Management, 1996, 37(Nos. 6-8):1229-1234.

Chavez et al., "Copper Sorption and Accumulation by the Extraradical Mycelium of Different *Glomus* spp. (*Arbuscular mycorrhizal fungi*) Isolated from the Same Polluted Soil", Plant and Soil, 2002; 240:287-297.

Fernandes et al., Rheological Behaviour of the Culture Medium During Growth of the Microalga Botryococcus Braunii, Bioresource Technology, 1991, 38:133-136.

Lee, "Calculation of Light Penetration Depth in Photobioreactors", Biotechnology and Bioprcoess Engineering, 1999, 4:78-81.

Liu et al., "Hypersalinity Enhances the Production of Extracellular Polymeric Substance (EPS) in the Texas Brown Tide Alga, *Aureoumbra lagunensis (pelagophyceae)*", Journal of Phycology, 2000, 36:71-77.

Meza et al., "Biofilm Formation by Algae as a Mechanism for Surviving on Mine Tailings", Environmental Toxicology and Chemistry, 2005, 24(3):573-581.

Olaizola, "Microalgal Removal of CO2 from Flue Gases: Changes in Medium pH and Flue Gas Composition Do Not Appear to Affect the Photochemical Yield of Microalgal Cultures", Biotechnology and Bioprocess Engineering, 2003, 8:360-367.

Otero et al, "Nostoc (Cyanophyceae Goes Nude: Extracellular Polysaccharides Serve as a Sink for Reducing Power Under Unbalanced C/N. Metabolism", Journal of Phycology, 2004, 40:74-81.

Otero et al., "Extracellular Polysaccharide Synthesis by Nostoc Strains as Affected by N Source and Light Intensity", Journal of Biotechnology, 2003, 102:143-152.

Ugwu et al., "Photobioreactors for Mass Cultivation of Algae", Bioresource Technology, 2008, 99:4021-4028.

Examination Report for EP12704896.5 dated Aug. 14, 2014.

Hu et al., "Microalgal triacylglycerols as feedstocks for biofuel production: perspectives and advances", The Plant Journal, 2008, 54:621-639.

Roessler, "Environmental control of glycerolipid metabolism in microalgae: commercial implications and future research directions", J. Phycol., 1990, 26:393-399.

Chisti, "Biodiesel from Microalgae", Biotechnology Advances 25, Science Direct, 2007, 294-306.

Domitrovic et al., "Variaciones Espaciales Y Temporales Del Fitoplancton En Un Lago Subtropical De Argentina", Rev. Brasil. Biol., 1998, 58(3): 359-382.

Khozin-Goldberg, et al., "Biosynthesis of Eicosapentaenoic Acid (EPA) in the Freshwater Eustigmatophyte *Monodus subterraneus*", Journal of Phycology, 2002, 38: 745-756.

Kim et al., "Red and Blue Photons Can Enhance the Production of Astaxanthin from Haematococcus Pluviatis", Algae, 2009, 24(2): 121-127.

Sheng et al., "Evaluation of Methods to Extract and Quantify Lipids from Synechocystis PCC 6803", Bioresource Technology, Jan. 2011, 102(2): 1697-1703.

Das et al., "Enhanced algae growth in both phototrophic and mixotrophic culture under blue light" Bioresource Technology, 2011, 102:3883-3887.

X Li, et al., "Effect of LED's red/blue light on the growth characteristic and lipid production of *Scenedesmus* sp. LX1", Feb. 2010, 31(2).

English Abstract for CN101864470, dated Oct. 20, 2010.

Zhang et al., "Research Progress of Cultivating and Developing PUFA from Microalgae", CHNFood, 2006, 27 (11):609.

English translation of Chinese Office Action for CN201280015125.0 dated May 18, 2015.

Bock et al., "Updating the genus *Dictyosphaerium* and description of *Mucidosphaerium gen. nov.* (Trebouxiophyceae) based on Morphological and Molecular Data," J. Phycol., 2011, 47: 638-652.

Garbayo et al., "Effect of abiotic stress on the production of lutein and beta-carotene by Chlamydomonas acidophila," Process Biochemistry, 2008, 43:1158-1161.

Lang et al., "Fatty acid profiles and their distribution patterns in microalgae: a comprehensive analysis of more than 2000 strains from the SAG culture collection," BMC Plant Biol., 2011, 11: 124.

Lang et al., Supplemental Data for "Fatty acid profiles and their distribution patterns in microalgae: a comprehensive analysis of more than 2000 strains from the SAG culture collection," BMC Plant Biol., 2011, 11: 124.

Liu et al., "Morphology and eicosapentaenoic acid production by *Monodus subterraneus*," Micron, 2005, 36:545-550.

Raja et al., "Exploitation of Dunaliella for beta-carotene production," Appl Microbiol Biotechnol, 2007, 74:517-523.

Notice of Reasons for Rejection for Japanese Application No. P2013-550958 dated Jan. 19, 2016.

Cultivation of Dictyospaerium chlorelloides in a 10-L Photobioreactor for tests on Exopolysaccharide production along with stress tests, RAWAT Consulting s.r.o., Brno for Algaecytes Ltd, Jul. 2010.

* cited by examiner

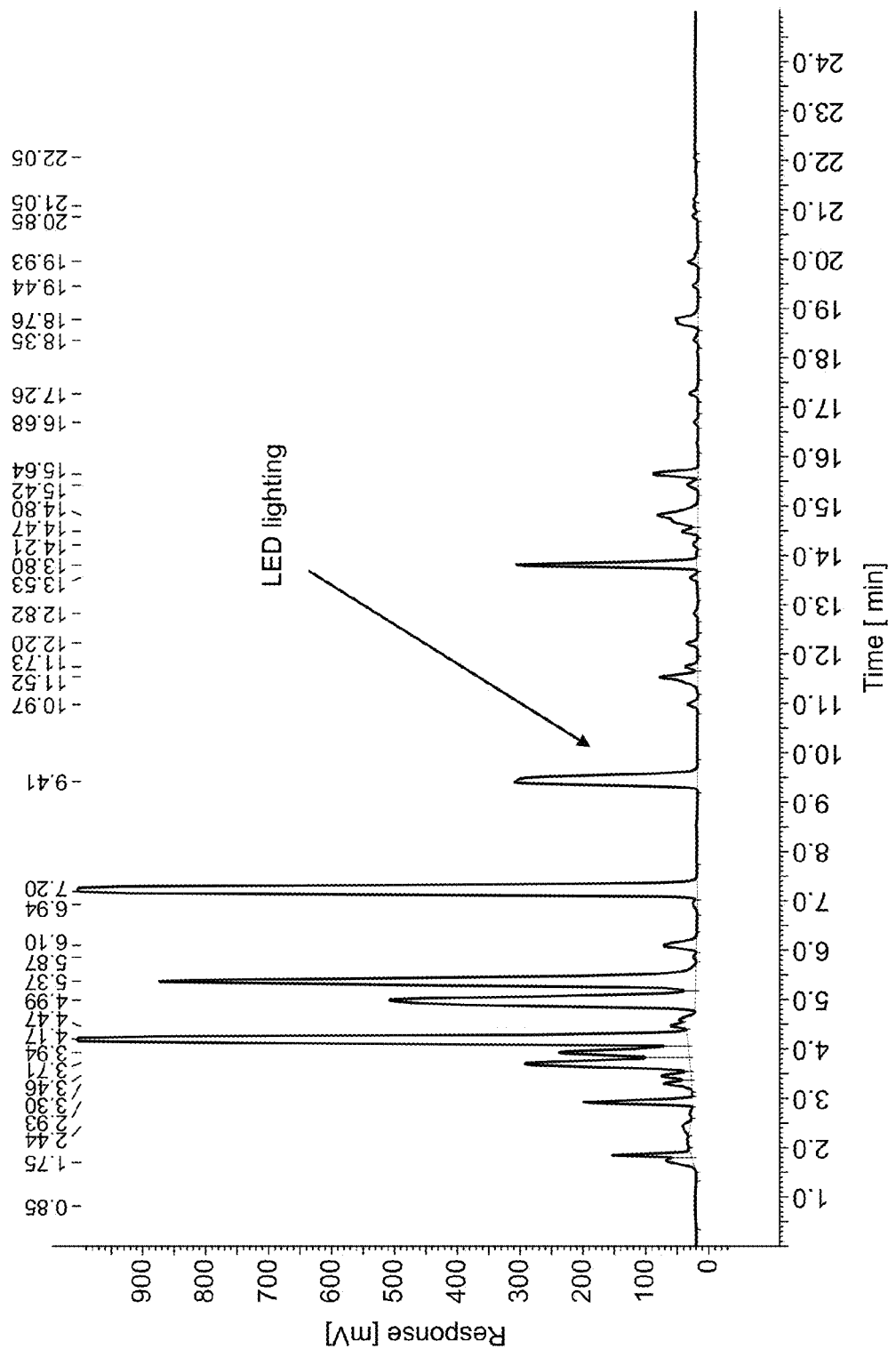
FIG. 1 Con't

| Micro-algae / Cyanobacteria | Carbohydrates | Lipids | Proteins | Combustion heat |
|---|---|---|---|---|
| Chlorella sp. ALG04 | 29±3% | 7±2% | 53±6% | 22,14MJ/kg |
| Synechococcus sp. ALG06 | 13±2% | 10±1% | 66±6% | 20,19MJ/kg |
| Trachydiscus sp. ALG01 | 27±4% | 24±4% | 43±8% | 22,56MJ/kg |

*FIG. 3*

| Fatty acid | | & of total fatty acid content |
|---|---|---|
| Lauric acid | C12:0 | 5.5 |
| Myristic acid | C14:0 | 23.4 |
| Palmitic acid | C16:0 | 10.1 |
| Stearic acic | C18:0 | 2.0 |
| Linoleic acid | C18:2n6 | 4.3 |
| Alpha Linolenic acid | C18:3n3 | 2.6 |
| Eicosapentaenoic acid | C20:5n3 | 27.0 |
| Behenic acid | C22:0 | 7.1 |

*FIG. 4*

| Micro-algae / Cyanobacteria | Carbohydrates | Lipids | Proteins | Combustion heat |
|---|---|---|---|---|
| Chlorella sp. ALG04 | 29±3% | 7±2% | 53±6% | 22,14MJ/kg |
| Dictyosphaerium chlorelloides. ALG03 | 38±4% | 5±2% | 41±7% | 20,10MJ/kg |
| Synechococcus sp. ALG06 | 13±2% | 10±1% | 66±6% | 20,19MJ/kg |
FIG. 10
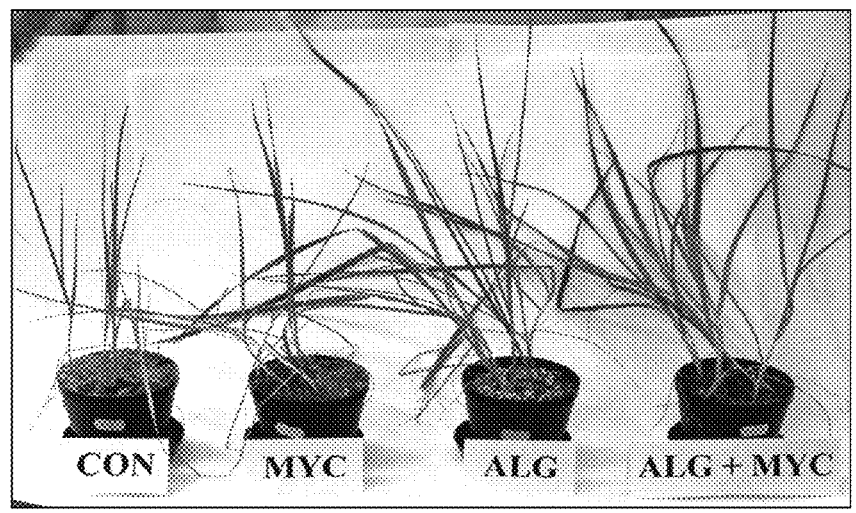
FIG. 11A
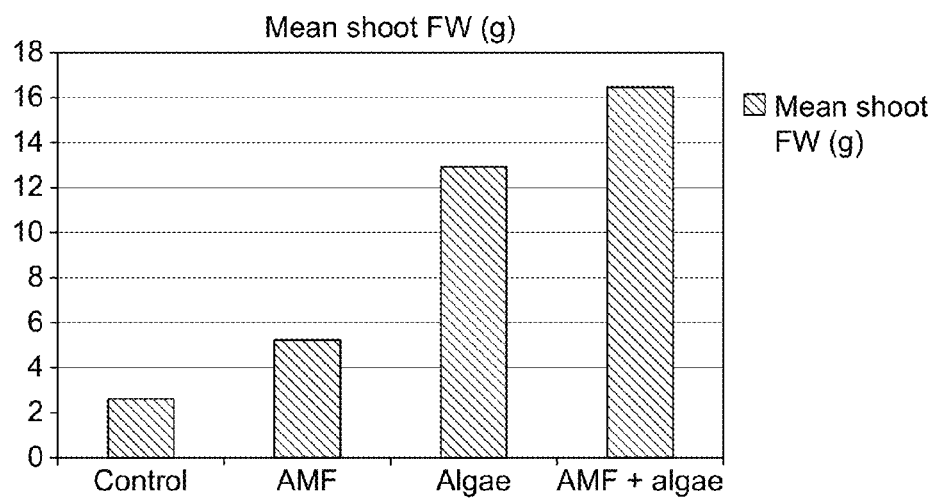
FIG. 11B

PROCESS FOR PRODUCTION OF MICROALGAE, CYANOBACTERIA AND METABOLITES THEREOF INCLUDING LIPIDS AND CARBOHYDRATES

CROSS REFERENCE TO RELATED APPLICATION

The present application is the U.S. national stage of International Application PCT/GB2012/050194, filed Jan. 30, 2013, which international application was published on Aug. 2, 2012, as International Publication No. WO 2012/101459. The international Application claims priority to British Patent Application Nos. 1101487.5, filed Jan. 28, 2011, and 1101489.1, filed Jan. 28, 2011, the contents of which are incorporated herein by reference in their entireties.

FIELD OF THE INVENTION

The present invention relates to a process for the production of microalgae, cyanobacteria and/or metabolites thereof. Particularly, although not exclusively, the present invention relates to a process wherein a microalgal or cyanobacterial culture is exposed to a stimulus in order to enhance the production of one or more metabolites. Also described herein, is a process for the production of microalgae and/or cyanobacteria comprising an adaptation stage wherein an algal/cyanobacterial culture is grown on a process water feedstock and/or under light emitting diodes (LEDs) emitting light within the spectrum of light wavelengths between around 400 nm and 700 nm, and a production phase, wherein the microalgae or cyanobacteria are grown on the same process water feedstock and/or under the same light conditions used in the adaptation stage.

The present invention integrates methods of cultivating lipid-forming micro-algae or cyanobacteria preferably in photobioreactor system(s), open ponds or other cultivating methods. It provides an integrated and continuous process for the production of algae biomass and conversion to high value by-products such as EPA or biofuels. A specific strain for use in the invention is also described, referred to herein as ALG02.

The present invention describes a process to enhance the exopolysaccharide (EPS) production of an unique microalgal strain (*Dictyosphaerium chlorelloides* ALG03) which is pre-tuned/adapted in culture for subsequent large scale production using defined LED lighting spectra along with industrial waste $CO_2$ and water as nutrient and energy for growth in photobioreactors (PBRs). Additionally it provides an integrated and continuous process for the production of algae biomass before/after carbohydrate extraction which can be used for other downstream purposes e.g. to enhance the nutrient availability and soil adhesion in the root zones of plants irrigated with sub-surface trickle irrigation; as biomass for anaerobic digester units or bioethanol plants or for biogas production. A specific strain for use in the invention is also described, referred to herein as ALG03.

BACKGROUND TO THE INVENTION

Algae are one of the fastest growing organisms on the earth. They can reproduce (bloom) within hours. They require only $CO_2$ and light to grow in either fresh, waste or sea water. In addition, elevated levels of nutrients (principally nitrogen and phosphates) found in industrial process water with other growth enhancing compounds can increase the biomass growth by algae (a).

Algae are being targeted for both future fuels and waste water treatment solutions in research ongoing across the globe. This is because algae, in the process of producing algae fuel, can sequester $CO_2$ from industrial sources and help sequester the nutrients (and some heavy metals) which are held within partially treated process water (b, c).

Algae and cyanobacteria are also valuable sources of metabolites, for example fatty acids including myristic acid, palmitic acid, palmitoleic acid, behenic acid, lauric acid, linoleic acid, alpha and gamma linolenic acid, stearic acid, arachidonic acid and eicosapentaenoic acid. Moreover, microalgal and cyanobacterial extracellular polymeric substances (polysaccharidic in nature) present unique biochemical properties that make them interesting from the biotechnological point of view. Cyanobacteria produce complex exopolysaccharides and their applications include food coating, emulsifying and gelling agents, flocculants, viscosifiers and hydrating agents in the food and non-food industries. There is also potential for their use as a source of novel compounds in soft tissue adhesives in healthcare (d). In the field of bioremediation, extra-cellular polysaccharides (EPSs) can remove toxic heavy metals from polluted soils and waters (e,f) and in waste water recycling of nutrients and other elements.

It is clear from the above that algae and cyanobacteria represent valuable resources in many different areas of technology, therefore the present inventors sought to develop new processes for the growth and production of such microorganisms.

SUMMARY OF THE INVENTION

In accordance with a first aspect of the invention, there is provided a process for the enhanced production of one or more metabolites in microalgae and/or cyanobacteria, said process comprising the steps of:
  (i) culturing a microalgal or cyanobacterial strain through a production phase;
  (ii) exposing the microalgal or cyanobacterial culture to a stimulus, wherein the stimulus comprises (a) a decrease in pH to a pH of no more than around pH 6, followed by an increase in pH to a pH of no less than around pH 7 and (b) an increase in light irradiance to at least 400 µmol/m$^2$/sec.

In accordance with a second aspect of the invention, there is provided a process for the production or growth of microalgae and/or cyanobacteria or the production of one or more metabolites derived therefrom, which process comprises:
  (i) an adaptation stage, comprising culturing microalgae or cyanobacteria:
    (a) on a process water feedstock and selection of those microalgae or cyanobacteria able to grow on the process water feedstock; and/or
    (b) under light emitting diodes (LEDs) emitting 2 peaks of red and blue light within the spectrum of light wavelengths between around 400 and 700 nm; and
  (ii) a production phase, comprising culturing the selected microalgae or cyanobacteria of (i) on the same process water feedstock used in the adaptation stage and/or under the same light conditions used in the adaption stage.

Also provided herein is a microorganism which is, or has the identifying characteristics of, a strain of *Chlorogibba allorgei* deposited with the Culture Collection of Algae and Protozoa (CCAP), managed by the Scottish Association for Marine Sciences (SAMS), Scottish Marine Institute (SMI), OBAN, Argyll PA37 IQA, United Kingdom, under the accession number CCAP 817/1 on Jan. 25, 2011 under the Budapest Treaty, or a mutant strain derived therefrom. The strain of *Chlorogibba allorgei* deposited under accession number CCAP 817/1 is also referred to herein as ALG02.

Further provided herein is a microorganism which is, or has the identifying characteristics of, a strain of *Dictyosphaerium chlorelloides* deposited with the Culture Collection of Algae and Protozoa (CCAP), managed by the Scottish Association for Marine Sciences (SAMS), Scottish Marine Institute (SMI), OBAN, Argyll PA37 IOA, United Kingdom, under the accession number CCAP 222/98 on Jan. 25, 2011 under the Budapest Treaty, or a mutant strain derived therefrom. The strain of *Dictyosphaerium chlorelloides* deposited wider accession number CCAP 222/98 is also referred to herein as ALG03.

The process provided herein may be for the enhanced production of micro-algae containing commercially valuable bio proteins, lipids and metabolites including Eicosapentaenoic acid (EPA), Myristic acid, Palmitic acid, Behenic Acid, Lauric acid, Linoleic acid, alpha Linolenic acid and Stearic acid. The process uses optimised light wavelengths for the culturing and production preferably in photobioreactors of lipid-rich micro-algae strains such as those within the phylum Chlorophyta and selected from the family Pleurochloridaceae. Industrial by-products such as spent process water and $CO_2$ are used as reclaimed sources of nutrients and carbon to tune/adapt the algae for enhanced growth using these inputs.

Also provided is a unique two stage process for the optimisation of the production of a commercially valuable exopolysaccharide in algae, in particular in *Dictyosphaerium chlorelloides* and may be applied to a specific micro-algal strain. The process takes place in a photobioreactor (PBR) system. The process takes advantage of industrial process Carbon Dioxide ($CO_2$)/water to culture the alga and increase growth rates under similar conditions in the scaled up PBR system. The process uses alga pre-adaptation culturing to tune the organism to the scaled up use of process water/$CO_2$ and LED lighting. This in turn enables the alga to produce elevated levels of an exopolysaccharide with commercial uses. The carbohydrate laden algal biomass can be employed in the irrigation of crops as a nutrient-rich and high carbon fertilizer or alternatively in downstream energy production (bioethanol production or other energy biomass systems e.g. Anaerobic digesters or fermentation vessels).

The invention provides a novel process of producing elevated yields of an exopolysaccharide from an adapted strain of *Dictyosphaerium chlorelloides* ALG03 which has been evolved to grow at high rates in a secondary treated waste water source under tuned LED lights. This treatment doubles the yield of extracellular polysaccharide from 38% to 77% observed in the lag phase of growth. The high percentage of polysaccharide produced can be moved to a downstream process where the polymer can be extracted for a variety of uses. The spent biomass remaining after carbohydrate extraction can be used for either animal feed (if pure water used in the bioreactor) or for energy production, for example, in Anaerobic Digesters, Fermentation processes or Pyrolysis systems.

The invention thus also relates to a specific (isolated) strain of algae belonging to the Dictyosphaeriaceae family and in particular the genus *Dictyosphaerium*, more specifically a strain of *Dictyosphaerium chlorelloides*. The strain was deposited with the Culture Collection of Algae and Protozoa under the accession number CCAP 222/98 and accepted on 25 Jan. 2011. This strain is shown herein to be useful in the production of specific metabolites.

The present invention further provides a novel process of using the produced algal biomass as a specific soil conditioner using subsurface drip irrigation systems (SDIs). The biomass grown within the remediated water passes into an irrigation holding tank ready for mixing with normal irrigation water and other compatible chemicals. The delivery of doses of the algal cells which have already absorbed phosphates and nitrates along with other nutrients from the waste or process water helps deliver a 'natural slow release' fertilizer to the root zone of the plants. It also increases the carbon in the soils and helps aggregate soil particles around the developing roots of the plants preventing soil erosion which is vital in arid zones.

These and other objects, which will become apparent during the following detailed description, have been achieved by the inventors' discovery that exopolysaccharide formation by pre-tuned/adapted algal strains can double the yields of the carbohydrate rich biopolymer by the manipulation of its pre-cultivation and management during growth within PBRs.

Enhanced HPLC FAME profiles under tuned LED lights compared with Fluorescent Lighting of a species of *Scenedesmus* (ALG05) which had 6 month pre-exposure to PAR LED lighting (400-700 nm) with 6 cycles of sub-culturing.

The HPLC (FAME) profiles obtained from algal strains cultured using LED PAR lighting only on 24 hour cycle for 6 months (6 sub-cultivations). Note the appearance of higher molecular weight fatty acids (arrowed in right image) compared with the same strain grown with fluorescent lighting (left image) of the same irradiance.

Figure 1:
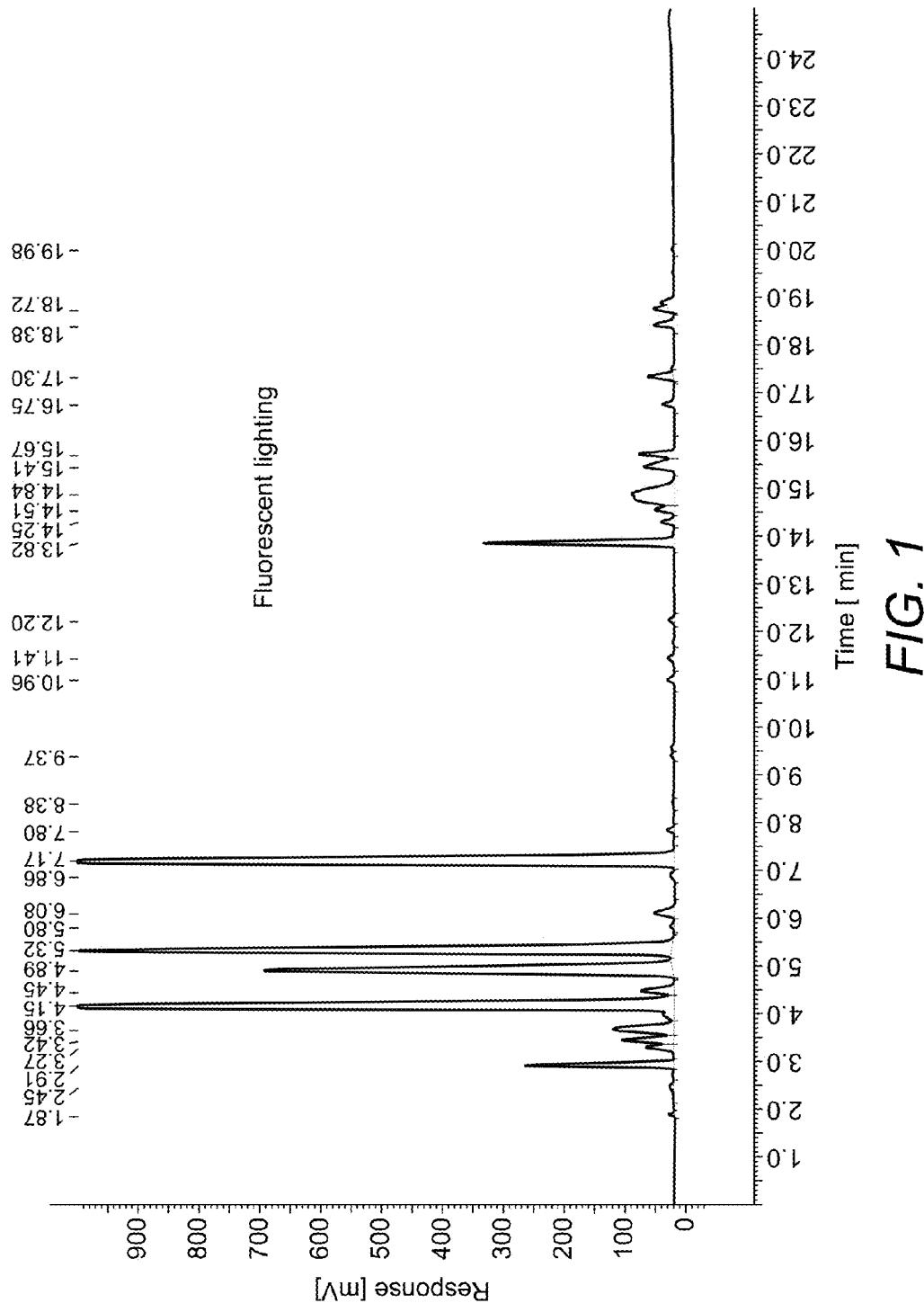
FIG. 1 LED Lighting Adaptation—FAME Profile
Figure 2:
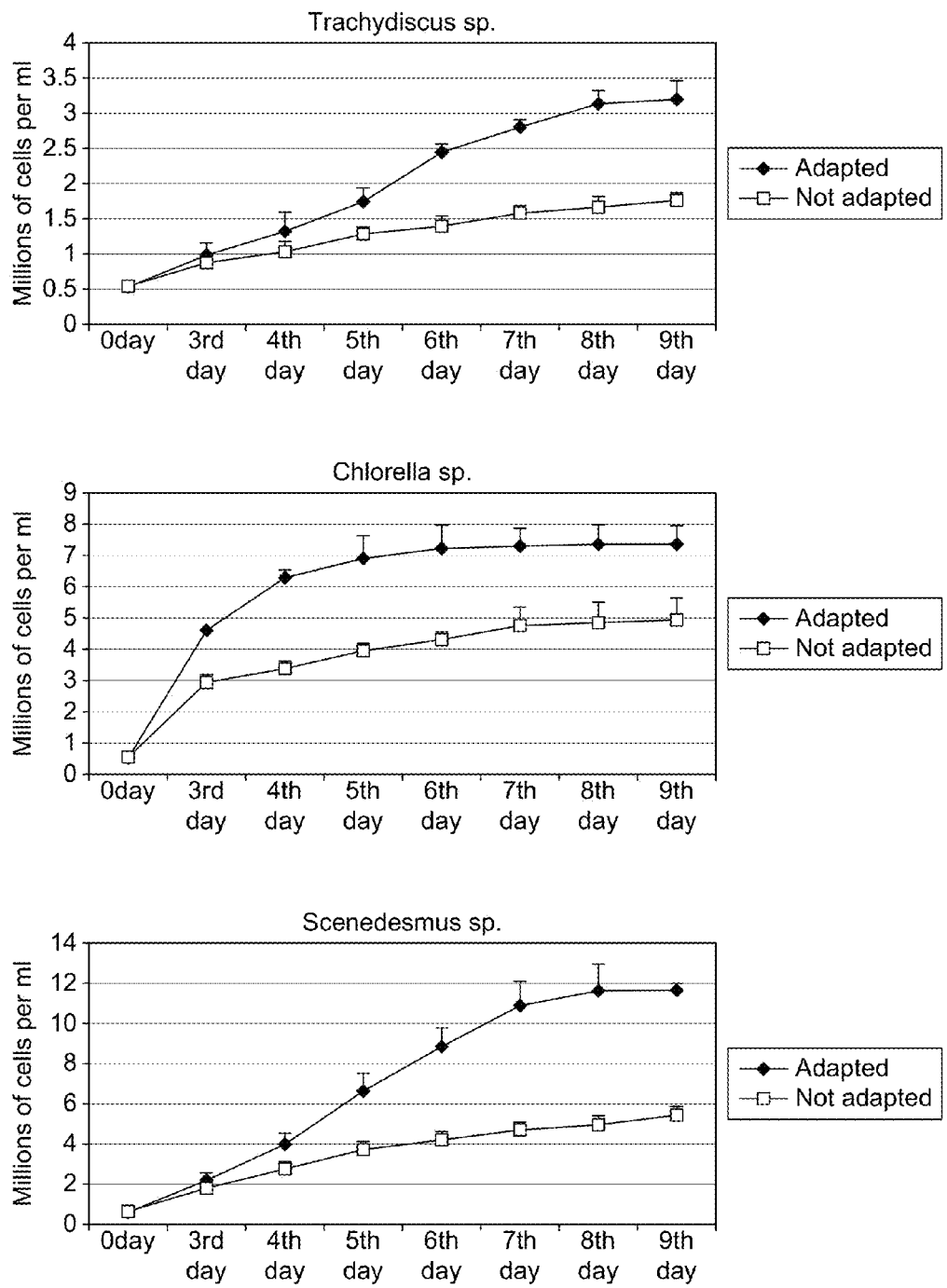

FIG. 2 Enhanced growth in treated process water with pre-cultivation

Increased growth of *Trachydiscus* sp. (ALG01), *Chlorella* sp. (ALG04) and *Scenedesmus* sp. (ALG05) by pre-cultivation with 6 months (6 cycles) of exposure to treated process water and tuned PAR LED lights (27° C. and 24 hours light).

Adapted cells were grown for 6 months in water from a process plant (Secondary treated) and re-cultivated each 4 weeks into fresh process water. Non-adapted cells were cultivated in standard 100% ZBB growth medium and re-cultivated every 4 weeks into new ZBB medium. Then both strains were grown for 9 days (until stationary phase) in new process water. Results show a clear adaptation to the process water environment and LED lighting by pre-adapted cells.

FIG. 3 Lipid contents of different strains

Comparison of Carbohydrate/Lipid/Protein production by strains in exponential growth phase and Calorific Values of Biomass. Cultures were harvested in the exponential growth phase.

FIG. 4 Production of eicosapentaenoic acid (EPA) in a strain of *Chlorogibba* sp. (ALG02)

Percentage content of principal fatty acids in biomass sample produced under sub-optimal growth conditions (no added $CO_2$ or PAR irradiance) and analysed by capillary chromatography. Other analyses for this strain and *Trachydiscus* sp. ALG01 grown using PAR light sources and added $CO_2$ have shown EPA percentages in the range 30-38% of total fatty acid contents. Significant levels of Palmitic and Myristic fatty acids in analyses have been detected under controlled PAR lighting.

Figure 5A:
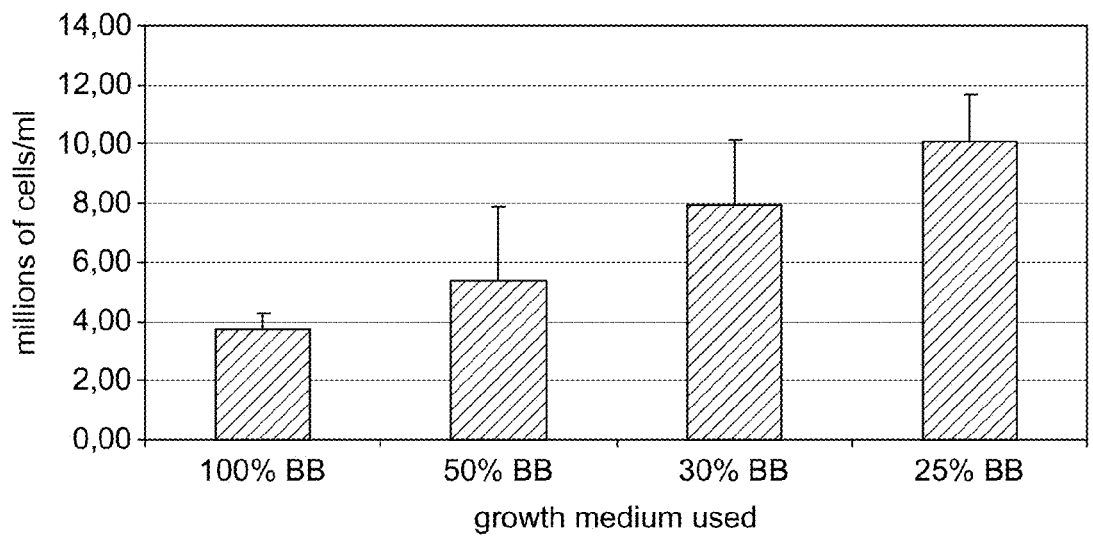

FIGS. 5A & B are graphs showing the results of experimental work carried out regarding the present invention and illustrating the relationship between nutrient concentrations and light levels and the growth of the algal strain *Dictyosphaerium chlorelloides* ALG03.

5A. Low Nutrient Level Requirements

Growth over 4 days in Bold's Basal Medium for algae shows that the alga needs relatively low levels of nutrients for optimal growth at 27° C. under optimal light irradiance.

5B. LED Light Irradiance Levels for Growth

Graph shows that alga grows best in low light over 7 days in 25% BB medium at 27° C.

Figure 6:
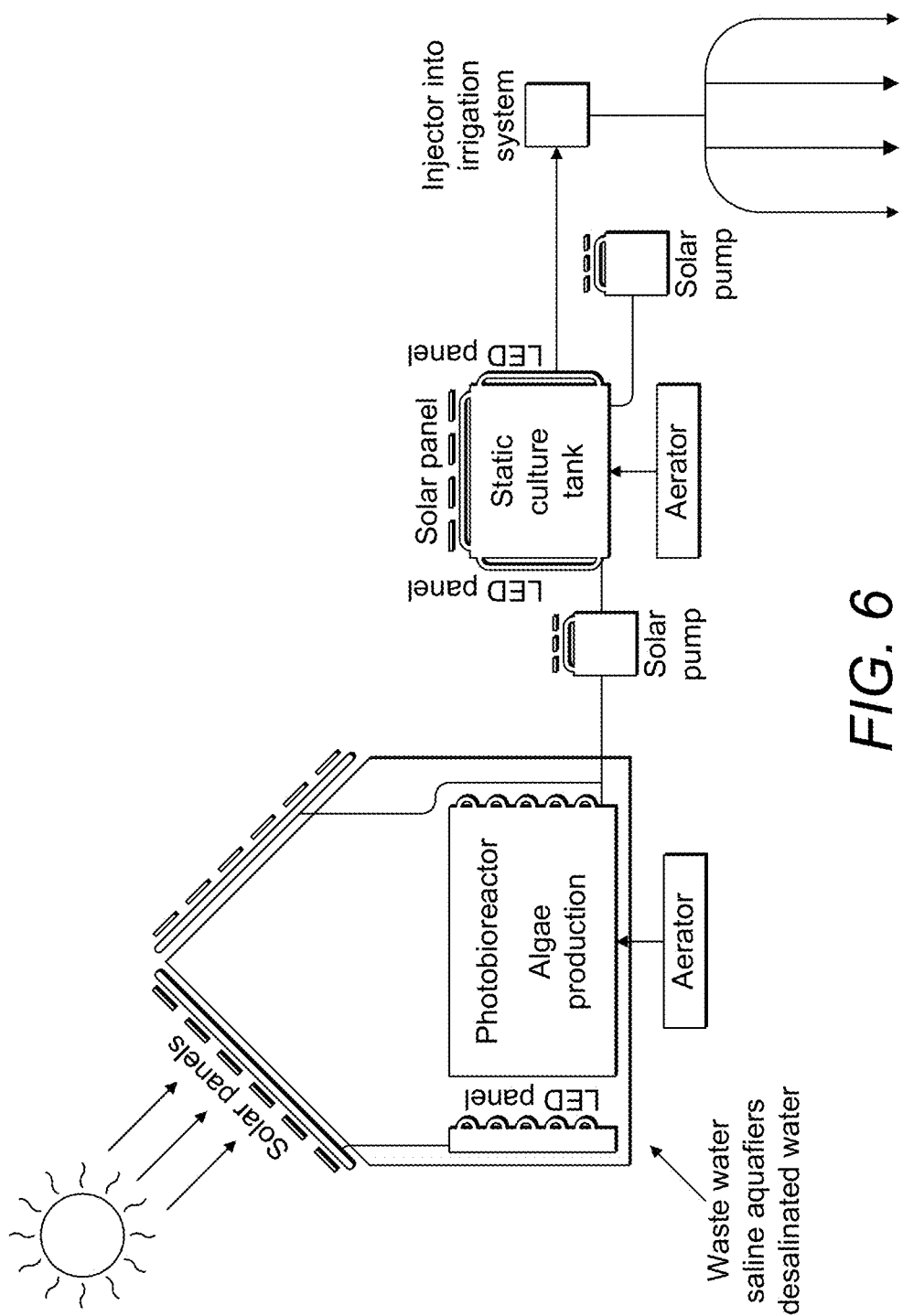

FIG. 6 is a schematic illustration of a system for producing algae biopolymer in accordance with the present invention for use in irrigation.

Figure 7:
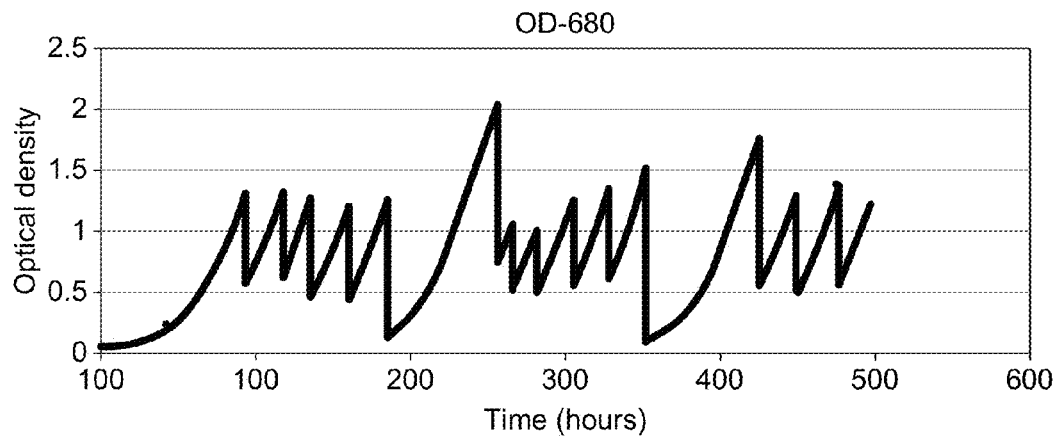

FIG. 7 is a graph showing the sequential harvesting of *Dictyosphaerium chlorelloides* ALG03. Biomass is shown as Optical Density (680 nm) readings in a PBR show that daily harvesting at 50% rates enables regrowth of the same biomass of *Dictyosphaerium chlorelloides* ALG03 within 24 hours when topped up with new growth medium.

Figure 8:
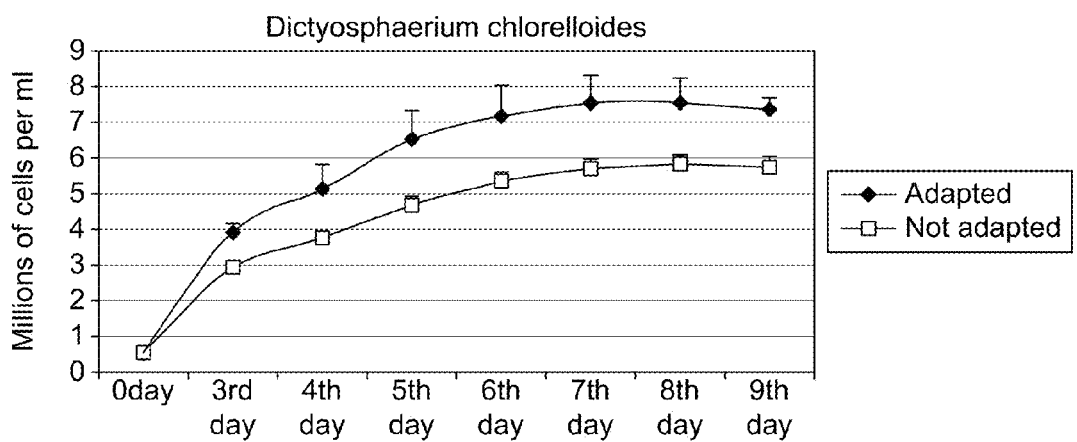

FIG. 8 shows the adaptation of the strain to waste water and LED lighting giving increased rates of growth compared with non-adapted strain.

Increased growth of *Dictyosphaerium chlorelloides* by physiological adaptation with 6 months (6 cycles) of exposure to waste water and tuned PAR LED lights (27° C. and 24 hours light).

Figure 9:
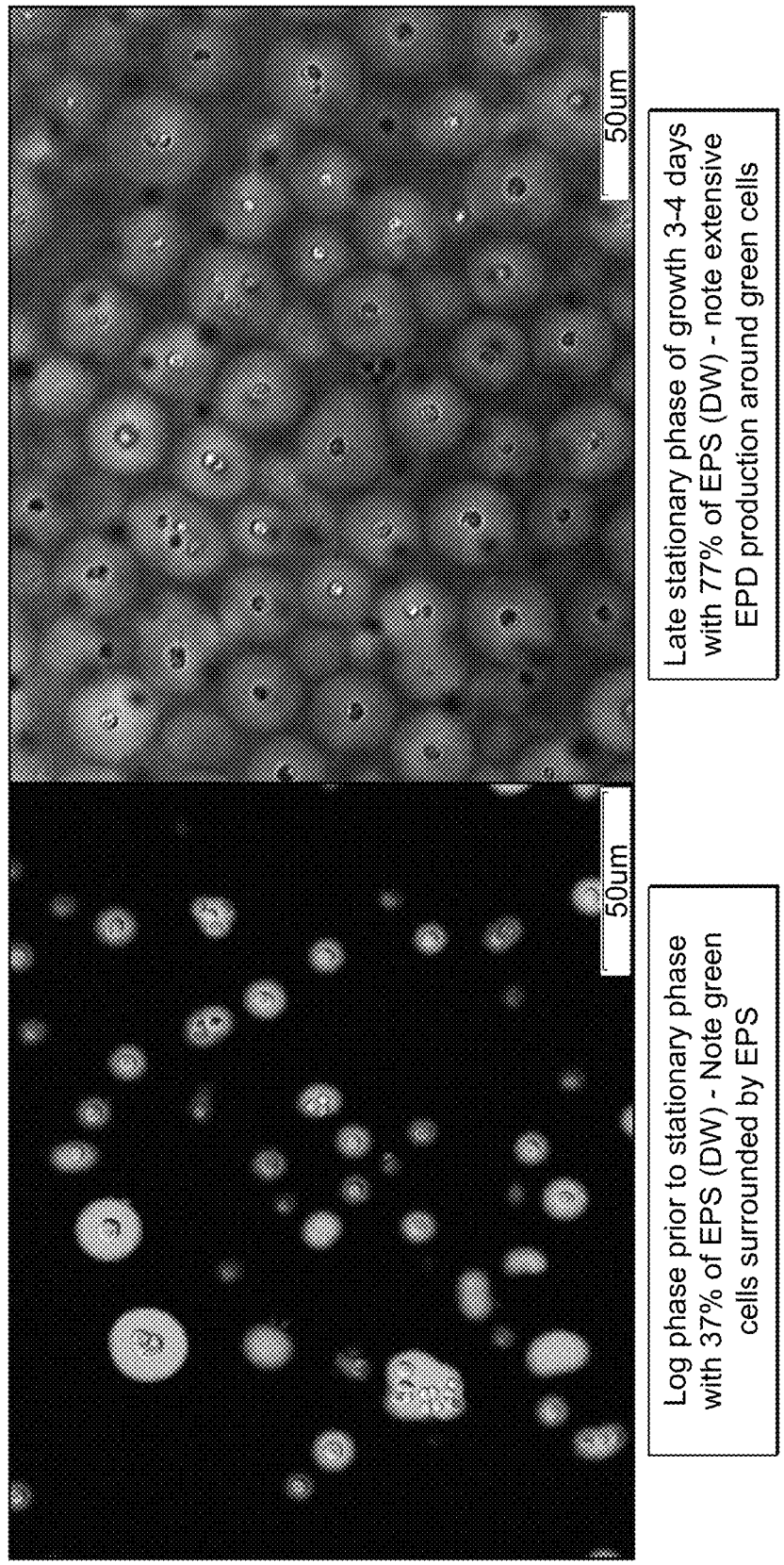

FIG. 9 shows the doubling of EPS following the end of the second stage cultivation (image on right).

FIG. 10 shows comparison of carbohydrate/lipid/protein contents of cells of 3 organisms and calorific values.

Comparison of Carbohydrate/Lipid/Protein production by a strain *Dictyosphaerium chlorelloides* ALG03 in log phase of growth and Calorific Values of Biomass. Cultures were harvested in the exponential growth phase.

FIG. 11 shows the results of using drip irrigation to grow leek in an infertile sandy soil in a greenhouse trial over a 12 week period. Panel (A) Photograph of leeks, from left to right, Control no algae; mycorrhizal fungal symbiont (mix of *Glomus* spp.) used at planting: algae used weekly; algae and mycorrhizal fungal symbiont; Panel (B) Graph of FW (g) for leeks of Panel (A).

DETAILED DESCRIPTION OF THE INVENTION

In a first aspect, the invention provides a process for the enhanced production of one or more metabolites in microalgae and/or cyanobacteria, said process comprising the steps of: (i) culturing a microalgal or cyanobacterial strain through a production phase; (ii) exposing the microalgal or cyanobacterial culture to a stimulus, wherein the stimulus comprises (a) a decrease in pH to a pH of no more than around pH 6 followed by an increase in pH to a pH of no less than around pH 7, and (b) an increase in light irradiance to at least 400 μmol/m²/sec.

In the context of the present invention, the term "culturing" is used to mean growth of one or more microalgal or cyanobacterial strains in any suitable media. Such media may include standard growth media as would be known to a person skilled in the art, for example Bold's basal medium or equivalent. In a preferred embodiment, microalgal or cyanobacterial strains are grown in process water, wherein the term "process water" includes process water emerging from industrial systems and domestic waste water. The process water may be treated prior to use (e.g. sterilised or not) and supplemented with nutrients such that the nutrient levels are within the ranges found in standard growth media.

The culture may be a batch, fed batch or an at least partially continuous culture (prior to stationary phase) in certain embodiments.

The Production Phase

Growth of the microalgal or cyanobacterial strain during the production phase typically occurs at an exponential rate. Therefore, in certain embodiments, the production phase corresponds to the exponential phase of growth of the culture.

The "exponential phase", also known as the "log phase" or "logarithmic phase", is a defined period during batch culture of microorganisms including microalgae and cyanobacteria, characterised by cell doubling. The number of new organisms appearing per unit time is proportional to the existing population. If growth is not limited, doubling will continue at a constant rate so both the number of cells and the rate of population increase doubles with each consecutive time period. The actual growth rate may vary depending on the strain of microorganism used and/or the growth conditions.

The environmental or culture conditions used during the production phase may be specifically selected so as to permit exponential growth of the microalgal or cyanobacterial strain that is being used.

In certain embodiments, the cell density for the microalgal or cyanobacterial strain at the point when exponential growth begins to cease, prior to the onset of the stationary phase, the end of the exponential phase of production, should be no less than $10^8$ cells per ml of culture media, and preferably between $10^7$ and $10^8$ cells per ml. The culture conditions used to achieve optimal growth of the culture or exponential growth of the culture may be selected from the following:

continuous artificial light of wavelength between around 400 nm and 700 nm; and/or continuous artificial light of between around 50 μmol/m²/sec and 200 μmol/m²/sec; and/or temperature between around 20° C. and 40° C.; and/or oxygen levels between around 500 mV and 800 mV; and/or pH between around pH6 and pH9.

It will be understood by a person of skill in the art that the culture conditions may be varied depending on the microalgal or cyanobacterial strain to be grown. Specific conditions are discussed herein for specific strains of the invention and such conditions can be used as a guide to be applied to other strains, as would be understood by one skilled in the art.

In preferred embodiments of the invention, culture or growth of the microalgal or cyanobacterial strain during the production phase occurs in a photobioreactor (PBR). As used herein, a photobioreactor should be taken to mean a bioreactor that incorporates one or more light sources to provide photonic energy input into the reactor. In preferred embodiments, the microalgae or cyanobacteria are grown in a system closed to the (external) environment. Preferred light sources include light emitting diodes (LEDs), and in particular, LEDs emitting PAR (photosynthetically active radiation in the range 400-700 nm) light. In certain embodiments, a PBR may be configured so as to include (highly tuned) LED light sources designed to provide 360 degree angle illumination from the center of the bioreactor so as to maximise the growth of different algal or cyanobacterial strains around the light source. In preferred embodiments, the light is delivered by LEDs emitting 2 peaks of red and blue light within the PAR spectrum 400-700 nm. In a preferred embodiment, the light is delivered by LEDs emitting a peak of red light in the range between around 500-665 nm, preferably around 660 nm, and a peak of blue light in the range between around 440-500 nm, preferably around 460 nm.

Wherein the production phase is carried out in a PBR, the density for the microalgal or cyanobacterial strain should be no less than 10% (v/v) of the volume of the PBR at the start of the production phase. In the same or alternative embodiments, the microalgal or cyanobacterial cultures are not exposed to natural sunlight.

The Stimulus

In the second step of the process of the invention, the microalgal or cyanobacterial culture is exposed to a stimulus, wherein the stimulus comprises, consists essentially of or consists of (a) a decrease in pH to a pH of no more than around pH 6 followed by an increase in pH to a pH of no less than around pH 7, and (b) an increase in light irradiance to at least around 400 $\mu$mol/m$^2$/sec.

The pH of the culture during the production phase will typically be in the region of around pH7-9, and therefore the stimulus may comprise a decrease in pH from a pH of between around pH7 and pH9 to a pH of between around pH3 and pH6, preferably between around pH5 and pH6. The pH of the culture may be decreased and subsequently increased by any suitable means known to one of skilled in the art, provided that the viability of the culture is not compromised. In a preferred embodiment, the pH is decreased by the addition of carbon dioxide, $CO_2$.

The light irradiance delivered to the culture during the production phase will typically be in the region of 50-200 $\mu$mol/m$^2$/sec and therefore the stimulus may comprise an increase in light irradiance from between around 50-200 $\mu$mol/m$^2$/sec to between around 400-2000 $\mu$mol/m$^2$/sec. The light source preferably comprises, consists essentially of or consists of one or more LEDs.

The microalgal or cyanobacterial culture is typically exposed to the stimulus once the culture has reached the peak of exponential phase growth. This peak occurs immediately prior to the onset of the stationary phase. The stationary phase is a well-defined period during batch culture of microorganisms including microalgae and cyanobacteria, wherein the growth rate of the culture slows, typically as a result of nutrient depletion and accumulation of toxic products. During this phase, the rate of microorganism growth is typically equal to the rate of microorganism death. It will be understood by one of skill in the art that any microalgal or cyanobacterial culture undergoes a transition from the peak of exponential growth into the stationary phase. The culture may be exposed to the stimulus any time during the peak of exponential phase growth or any time during the transition from the exponential phase into the stationary phase.

The growth rate of microalgae or cyanobacteria can be monitored throughout the production phase, for example using sampling techniques such as cell counts or by measuring the levels of chlorophyll a in the culture. Cell numbers may be determined using spectrophotometric sampling of the culture, for example by taking readings at around OD 680 nm. These measures can be used to identify the exponential phase of growth, the peak of exponential phase growth and the time at which the culture starts to enter the stationary phase of growth. Any suitable technique may be employed.

The stimulus comprises as a minimum a decrease in pH to a pH of no more than around pH 6 followed by an increase in pH to a pH of no less than around pH 7, and an increase in light irradiance to at least 400 $\mu$mol/m$^2$/sec. The stimulus may additionally comprise addition of a carbon source, wherein the carbon source is $CO_2$ in its various forms.

In preferred embodiments, the decrease and subsequent increase in pH precedes the increase in light irradiance. The pH may be lowered to a pH of no more than around pH 6, preferably between around pH5 and pH6, for a period of between around 30 minutes and around 2 hours. The pH may subsequently be increased to a pH of between around pH6 and pH9, preferably between around pH7 and pH9. The pH may be elevated using any suitable means, provided that this does not compromise the viability of the culture. Generally, pH is restored to pre-stimulus levels.

In certain embodiments, the microalgal or cyanobacterial culture is cultured for a further period of growth of at least around 12, 24, 36, 48 etc hours after exposure to the stimulus commences. In embodiments wherein the pH is decreased for a period of between around 30 minutes and 2 hours, and subsequently elevated, for example to pre-stimulus levels, the period of culture following exposure to the stimulus may be calculated from the time of the initial pH decrease, or from the time the pH is restored and the irradiance is subsequently increased.

Production of Metabolites

One effect of exposure of the microalgal or cyanobacterial strain to the stimulus is to induce or promote production of particular metabolites within the microalgae or cyanobacteria. It has been noted by the current inventors that the exposure of certain microalgal and/or cyanobacterial strains to the stimulus as defined herein leads to the production of large quantities of particular metabolites, the particular metabolite being dependent on the strain of microorganism used. The purpose of carrying out the claimed process described above is thus to enhance production of one or more metabolites in microalgal and/or cyanobacterial cells. Such metabolites are typically harvested following the further period of growth after the culture has been exposed to the stimulus. Metabolites may be harvested, purified and/or analysed using any suitable means known to those skilled in the art, for example, as described in Bligh, E. G. and Dyer, W. J. 1959. A rapid method for total lipid extraction and purification. *Can. J. Biochem. Physiol.* 37:911-917.

Lipids may also be harvested/analysed according to industrial standard procedures such as supercritical $CO_2$, variants on solvent extractions, fractional distillation and chromatography, or according to the following protocol:

25 mg of sample of algae product is mixed with the internal standard if used to GC-MS measurements in culture tubes. Add 1.5 ml of 0.5N Sodium hydroxide in methanol, cap tubes and heat at 100° C. for 5 mins. Allow to cool and add 2 ml BF3/methanol reagent, cap tubes, mix and heat at 100° C. for 30 mins. Allow to cool and 2 ml of iso-hexane+BHT, and then 5 ml of saturated Sodium Chloride, cap tube and shake for 30 secs vigorously. Cool to room temperature and allow layers to separate. The upper isohexane layer is put through a short column of anhydrous sodium sulphate and collected. The aqueous layer is extracted with 2 ml of iso-hexane+(Butylated hydroxytoluene) BHT and the upper isohexane layer is placed through the anhydrous sodium sulphate column and the solvent collected with the other sample. The column is washed with 2 ml of iso-hexane+BHT and also placed in the same sample tube.

Polysaccharides may be analysed by chromatography techniques available to those skilled in the art. The analysis of carbohydrates and sugar alcohols may be analysed in microalgal bio-mass extracts by high pH anion exchange chromatography (HPAE) followed by electrochemical detection (IPAD) and mass spectrometry detection in parallel. In a preferred embodiment, the sample extract is analysed using a modular ICS-5000 system coupled to a MSQ Plus mass spectrometer. The analytes are separated on a CARBOPAC™ MAl column using isocratic condition. After the analytical column, the columns effluent is split so half of it flows through to the amperometry cell, where integrated and pulsed amperometric detection (IPAD) is accomplished, while the other half is continuously desalted using a membrane based desalting device (ASRS). The neutralized effluent is then mixed with an aqueous solution of lithium chloride in order to facilitate the carbohydrate detection in the MS as their lithium adducts.

The spent biomass may, in turn, be utilised for a variety of applications including, but not limited to ruminant feed, cattle feed, aquaculture, poultry feed, Bioethanol production carbohydrate fraction of the biomass and extraction of valuable amino acids from proteins.

The process described herein may be used to enhance the production of any metabolite found within microalgal and/or cyanobacterial stains. In certain embodiments of the invention, the process is used for the enhanced production of lipids including, but not limited to a fatty acid selected from myristic acid, palmitic acid, palmitoleic acid, behenic acid, lauric acid, linoleic acid, alpha and gamma linolenic acid, stearic acid, arachidonic acid and eicosapentaenoic acid. In a preferred embodiment, the process of the invention is for the enhanced production of eicosapentaenoic acid (EPA). The process described herein may be used in particular to obtain desired fatty acid profiles in the cultured microalgal or cyanobacterial strains, for example to optimise EPA production in EPA-producing strains. Fatty acids produced by means of the process described herein may for example, be used in the food sector, for liquid biofuel production, for cosmetic ingredients.

In certain embodiments of the invention, the process is used for the enhanced production of carbohydrates. In a preferred embodiment, the process of the invention is for the enhanced production of exopolysaccharide (EPS).

Microalgae/Cyanobacteria

The microalgae or cyanobacteria for use in conjunction with the process of the present invention may be selected from any suitable algal or cyanobacterial strains. Suitable microalgal strains may be selected from the following:— green microalgae; freshwater microalgae; the phylum Chlorophyta; the family Pleurochloridaceae; *Trachydiscus* sp; *Chlorogibba* sp.; and *Dictyosphaerium chlorelloides*. Suitable cyanobacterial strains may be selected from the following:—the order Chroococcales; the genera *Synechocystis* or *Synechoccocus*.

In embodiments wherein the process is to be used for the enhanced production of eicosapentaenoic acid, it is preferred that the microalgal strain is selected from *Trachydiscus* sp and *Chlorogibba* sp., and is in particular, the strain of *Chlorogibba allorgei* deposited with the Culture Collection of Algae and Protozoa under the accession number CCAP 817/1 (also referred to herein as ALG02), or a mutant strain derived therefrom.

In embodiments wherein the process is to be used for the enhanced production of exopolysaccharide, it is preferred that the microalgal strain is selected from *Dictyosphaerium chlorelloides*, and is in particular, the strain of *Dictyosphaerium chlorelloides* deposited with the Culture Collection of Algae and Protozoa under the accession number CCAP 222/98 (also referred to herein as ALG03), or a mutant strain derived therefrom.

As used herein, the term "mutant strain" is intended to mean a strain derived from the original microalgal and/or cyanobacterial strain, which retains the characteristics of the originating strain insofar as such characteristics relate to the metabolite profile produced when the strain is exposed to a stimulus in accordance with the process of the invention, described above.

The microalgae and/or cyanobacteria for use in conjunction with the process of the present invention may have been pre-selected, for example on the basis of optimal growth under the same culture conditions as used during the production phase. This pre-selection or adaptation stage, which may precede the steps of the process detailed above, is described in more detail in accordance with the second aspect of the present invention described herein below. All embodiments described hereinbelow are applicable to the other aspects of the invention.

Thus, in accordance with a second aspect of the invention, there is provided a process for the production or growth of microalgae and/or cyanobacteria, or the production of at least one metabolite derived therefrom, which process comprises:
  (i) an adaptation stage, comprising culturing microalgae or cyanobacteria:
    (a) on a process water feedstock and selection of those microalgae or cyanobacteria able to grow on the process water feedstock; and/or
    (b) under light emitting diodes (LEDs) emitting 2 peaks of red and blue light within the spectrum of light wavelengths between around 400 and 700 nm; and
  (ii) a production phase, comprising culturing the selected microalgae or cyanobacteria of (i) on the same process water feedstock used in the adaptation stage and/or under the same light conditions used in the adaption stage.

Adaptation

The process water feedstock may be sourced from industrial process systems or domestic waste water systems. Important algal growth nutrients such as nitrates and phosphates are typically present in said feedstock. Other algal stimulants may also be present such as minor elements and vitamins. The Food, Soft Drinks and Brewery sectors have many such process water streams suitable. Other less nutrient rich freshwater sources may be used if nutrients are added equivalent to the levels used in standard growth media.

The microalgae or cyanobacteria are typically cultured in the process water feedstock during the adaptation stage under optimal culture conditions including, but not limited to the following:
  continuous artificial light of wavelength between around 400 nm and 700 nm; and/or
  continuous artificial light of between around 50 µmol/m²/sec and 200 µmol/m²/sec; and/or
  temperature between around 20° C. and 29° C.; and/or
  pH between around pH7 and pH9.

The process water may be pre-conditioned, for example so as to reduce particulates. Growth of microalgae or cyanobacteria during the adaptation stage may be carried out using Erlenmeyer flasks (100-500 ml) or preparative photobioreactors. Light may be delivered by LED sources or other non-natural light. In a preferred embodiment, the light is delivered by LEDs emitting 2 peaks of red and blue light within the PAR spectrum 400-700 nm. In a further preferred embodiment, the light is delivered by LEDs emitting a peak of red light in the range between around 500-665 nm, preferably around 660 nm, and a peak of blue light in the range between around 440-500 nm, preferably around 460 nm.

In certain embodiments, the aim of the adaptation stage is to identify microalgal or cyanobacterial strains that are capable of growing on the process water feedstock to be used in the production phase of the process.

Alternatively, or in addition, the light may be used to adapt or "tune" the microalgae or cyanobacteria to the conditions to be used in the production phase, preferably so as to optimise growth during the production phase. In a preferred embodiment, the adaptation phase involves growth of algae and/or cyanobacteria under LEDs emitting 2 peaks of red and blue light within the PAR spectrum 400-700 nm. In a further preferred embodiment, the light is delivered by LEDs emitting a peak of red light in the range between around 500-665 nm, preferably around 660 nm, and a peak of blue light in the range between around 440-500 nm, preferably around 460 nm.

The adaptation stage may involve culturing the microalgal or cyanobacterial strains for a period of at least around 2, 3, 4, 5, 6 months, preferably at least around 3 months. The adaptation stage may involve culturing the microalgal or cyanobacterial strains for at least around 2, 3, 4, 5, 6, 7, 8 generations of growth, preferably at least around 6 generations of growth. In embodiments wherein the microalgae or cyanobacteria are grown for several months or for at least 2 generations of growth, the microalgae or cyanobacteria may be sub-cultured, wherein sub-culturing is intended to mean the transfer of some or all of the culture to a new growth medium. In a preferred embodiment, the microalgae or cyanobacteria are sub-cultured once per month or once every 4 weeks.

Once a microalgal or cyanobacterial strain has been selected in accordance with the adaptation stage described above, the second step of the process is the production phase, which comprises culturing the selected microalgae or cyanobacteria on the same process water feedstock and/or under the same light conditions used in the adaption stage.

The term "the same" process water feedstock is intended to mean process water from the same batch i.e. with the same characteristics, as used for the adaptation stage, rather than the exact same media used for growth of cells during the adaptation stage.

The production phase of the second aspect of the invention may be carried out in accordance with any of the embodiments of the production phase as described above for the process of the first aspect. For example, growth of the adapted microalgal or cyanobacterial strain may be carried out under conditions that permit exponential growth. Moreover, growth during the production phase is preferably carried out in a photobioreactor according to the above definitions. The conditions used in the production phase may mirror the conditions used in the adaptation stage. Thus, in addition to utilising process water as the feedstock, the adaptation may extend to additional environmental conditions, as outlined above (light wavelength, irradiance levels, temperature, pH etc.). More specifically, adaptation may be to use of LED lighting as described herein. In a preferred embodiment, adaptation is to LED lighting delivered at 2 peaks of red and blue light within the PAR spectrum 400-700 nm. In a further preferred embodiment, the light is delivered by LEDs emitting a peak of red light in the range between around 500-665 nm, preferably around 660 nm, and a peak of blue light in the range between around 440-500 nm, preferably around 460 nm.

In certain embodiments, the production phase may be followed by a step comprising exposure of the microalgal or cyanobacterial culture to a stimulus to enhance production of metabolites. All embodiments of the stimulus described above in the context of the first aspect of the invention apply mutatis mutandis to the process of the second aspect of the invention. Moreover, the microalgal and/or cyanobacterial strains for use in accordance with the process of the second aspect of the invention may be selected from any of the microalgal and/or cyanobacterial phyla, orders, families and/or species already described above.

The process of the second aspect of the invention may be used to enhance the production of microalgal and/or cyanobacterial biomass. Such biomass may be used in applications such as the production of biofuel, biodiesel, gasoline, kerosene or for use as a soil conditioner or biofertilizer, including in subsurface irrigation systems, as described herein below. Alternatively, or in addition, the process may be used for the production of metabolites, including but not limited to the enhanced production of lipids and/or carbohydrates. In preferred embodiments, the process is for the enhanced production of eicosapentaenoic acid. In a further preferred embodiment, the process is for the enhanced production of exopolysaccharide.

In a further aspect of the invention, there is provided a microorganism which is, or has the identifying characteristics of, a strain of *Chlorogibba allorgei* deposited with the Culture Collection of Algae and Protozoa under the accession number CCAP 817/1, or a mutant strain derived therefrom.

In a yet further aspect, there is provided a microorganism which is, or has the identifying characteristics of, a strain of *Dictyosphaerium chlorelloides* deposited with the Culture Collection of Algae and Protozoa under the accession number CCAP 222/98, or a mutant strain derived therefrom.

The present invention describes a process for the production of lipids and metabolites of Eicosapentaenoic acid, Myristic acid, Palmitic acid, Behenic Acid, Lauric acid, Linoleic acid, alpha Linolenic acid and Stearic acid and the like from algae belonging to the Pleurochloridaceae family (e.g. *Trachydiscus* sp. and *Chlorogibba* sp.). Accordingly, the invention provides a process for priming and selecting adapted cells of the said algae cultures ready for bioreactor and/or other cultivating conditions used to produce algae biomass products containing lipids and metabolites described herein. More particularly the present invention provides a process for the production of and/or increasing the yields of certain lipids containing fatty acids. The method may comprise a method of preparing algae belonging to the Pleurochloridaceae family and containing the aforementioned lipids and fatty acids by increasing photosynthetic efficiency, nutrient adjustment and metabolic activity for downstream production of biodiesel, gasoline, kerosene and other high value chemicals. Also the present invention provides a process for obtaining desired fatty acid profiles in the Eicosapentaenoic acid forming algal strains. This process allows for optimisation for either Eicosapentaenoic acid production for the food sector or saturated fatty acids or fatty acids—Myristic acid, Palmitic acid, Behenic acid, or Lauric acid, Linoleic acid, alpha Linolenic acid and Stearic acid and the like for liquid biofuel(s) production or for cosmetic ingredients by adjusting certain nutrient levels (including Nitrogen and Sulphur) in the growth medium along with altered light irradiance levels. The present invention also provides a method for preparing species from the cyanobacteria order Chroococcales in the genera *Synechocystis* and *Synechoccocus* containing some or all of the the aforementioned lipids and fatty acids by increasing photosynthetic efficiency and metabolic activity. The present invention further provides a process for obtaining specific production of fatty acids in the lipids by tuning photosynthetic efficiency in the presence of select bands within the Photosynthetically Active Radiation (PAR) wavelengths using continuous light.

The invention also relates to a specific (isolated) strain of algae belonging to the Pleurochloridaceae family and in particular the genus *Chlorogibba*, more specifically a strain of *Chlorogibba allorgei*. The strain was deposited with the Culture Collection of Algae and Protozoa under the accession number CCAP 817/1 and accepted on 25 Jan. 2011. This strain is shown herein to be useful in the production of specific metabolites.

The present invention further provides a process for the production of algal biomass product containing Eicosapentaenoic acid and the aforementioned lipids, fatty acids and metabolites thereof; suitable for downstream production of bio-diesel, gasoline, kerosene and other such liquid biofuels and high value industrial chemicals comprising the steps of:

a) an upstream culturing stage which is used to isolate, sub-culture and prepare tuned algae belonging to species within the Chlorophyta including specifically the EPA-rich Pleurochloridaceae family and the cyanobacteria order Chroococcales in the genera *Synechocystis* and *Synechoccocus* using tuned continuous light PAR wavelengths and process water stress. The algae belonging to the Pleurochloridaceae family and the cyanobacteria order Chroococcales in the genera *Synechocystis* and *Synechoccocus* are now ready for scale up in bioreactors using similar light delivery and water sources. The results show that up to a twofold increase in growth rates compared with the same cultures grown in normal water with added nutrients and daylight or fluorescent lighting can be expected across different strains.

b) a Photobiobioreactor stage in which algae belonging to the Chlorophyta, the Pleurochloridaceae family or the cyanobacteria order Chroococcales in the genera *Synechocystis* and *Synechoccocus* are grown within industrial process water, +/−nutrients (100% standard BB growth medium which comprises $NaNO_3$ (0.25 g/L); $CaCl_2.2H_2O$ (0.025 g/L); $MgSO_4.7H_2O$ (0.075 g/L); $K_2HPO_4$ (0.075 g/L); NaCl (0.025 g/L); $KH_2PO_4$ (0.175 g/L); $FeSO_4.7H_2O$ (4.98 mg/L); $H_2SO_4$ (0.01 µl/L); $H_3BO_3$ (0.1142 g/L); $ZnSO_4.7H_2O$ (0.00882 g/L); $MnCl_2.4H_2O$ (0.00144 g/L); $MoO_3$ (0.00071 g/L); $CuSO_4.5H_2O$ (0.00157 g/L); $Co(NO_3)_2.6H_2O$ (0.00049 g/L); EDTA (0.005 g/L); KOH (0.031 g/L)), specific PAR light wavelengths and irradiance levels in a continuous flow system is maintained in exponential growth phase to allow daily harvesting of a set proportion of the biomass product. The biomass product containing aforementioned lipids, fatty acids and metabolites thereof and bio proteins belonging to the Pleurochloridaceae family and the cyanobacteria order Chroococcales in the genera *Synechocystis* and *Synechoccocus*. The bioreactor is replenished with process water or process water amended with nutrients to allow the algal cell density to recover to the exponential growth stage before the next harvest.

Generally algae contain about 7 to 60% weight by weight lipid content relative to the total weight of dry algae. In the case of algae belonging to the Pleurochloridaceae family, Eicosapentaenoic acid comprises 25 to 40% of the total fatty acid in the lipid and the remaining fatty acids are mainly the aforementioned saturated or unsaturated fatty acids. Hence algae belonging to the Pleurochloridaceae family possess greater amounts of EPA than traditional sources derived from fish oils.

According to the embodiment of the present invention, lipids and metabolites of Eicosapentaenoic acid, Myristic acid, Palmitic acid, Behenic Acid, Lauric acid, Linoleic acid, alpha Linolenic acid and Stearic acid and the like belonging to the Pleurochloridaceae family can be found to be present as free fatty acids and/or in situ in the growth medium and/or obtained from the wet algal biomass product and/or algal homogenate and/or the algae following lyophilisation or air drying and extracted in the presence of a suitable organic solvent and/or sonicated or using supercritical $CO_2$.

In certain embodiments of the invention when growth media (using water for remediation or nutrient amended water) flows through the bioreactor with the algae, it is exposed to tuned sets of banks of dimmable LED lights internally or externally to the bioreactor comprising unique patterns of Red and Blue light emitting diodes (LEDs) which are set to operate at different wavelengths depending on the algal strain. The angulation of the LEDs is optimised for maximal delivery of irradiance to the cultures of algae growing within the PBR to promote and maintain the exponential growth phase of the algae. The algae biomass is monitored for cell density but also for the lipid/fatty acid contents to check that they have reached the target levels. The biomass is then dewatered and passed to the appropriate downstream process for biofuels or high value fatty acids are to be extracted. The spent biomass remaining can be used for either animal feed (if pure water is used in the bioreactor) or for energy production in Anaerobic Digesters (AD) or pyrolysis systems.

Bioreactor

This present invention provides an integrated process of using any combination of standard or renewable energies such as solar, wind, hydro, geothermal, and thermal and/or other renewable energies to power a photo-bioreactor and produce continual high yields of algae biomass. By using efficient and cost effective methods the algae biomass is refined further to produce biodiesel, biokerosene, gasoline, ethanol and other valuable co-products.

The system encompasses highly tuned LED light sources which are designed to maximise the growth of different algae strains. The system encompasses, but is not limited to, inclusion of highly tuned LED light sources which are designed to provide 360 degree angle illumination from the centre of a bioreactor to maximise the growth of different algae strains (growing around the light source).

Sources of Energy

The system can be self-powered using energy from solar, wind, hydro, geothermal and thermal and/or renewable energies. These various energy sources are managed through a commercial power management system which uses a scalable storage facility (such as a battery bank) to store and supply energy.

The temperature of the process is controlled by two means: the heating of the water through the supply of process water naturally emerging from industrial systems or domestic waste water and regulated by thermostats or heat exchangers or managed through an automated process control unit.

Low Energy Light Sources

The process employs a wide range of low voltage lights (such as LEDs as well as other unique light emitting sources) which is powered by a combination of standard and/or renewable energy sources, where the lights are tuned to optimise the growth of algae without compromising the lipid or other commercially valuable by-products.

In the preferred embodiments a set of lights, emitting light covering wavelengths with a precise angle of beam emissions within the Photosynthetically Active Radiation (PAR) wavelengths from 400-700 nm, is fitted internally or externally to the PBR. This helps to stimulate the algae to maximise the biomass growth at a cost effective production rate.

The algae have been selected from prior environment adaptive conditioning, using specific light sources and wavelengths, process water, temperature and pH management, to yield strains capable of optimal growth under reduced energy inputs.

In an embodiment the present invention provides a novel process for enhancing the exopolysaccharide (EPS) of the alga *Dictyosphaerium chlorelloides* ALG03 within any photobioreactor system. This comprises (a) a pre-cultivation to adapt the strain to tuned LED lighting within the photosynthetically active readiation (PAR) wavelengths and industrial process water conditions (e.g. secondary treated process water); (b) growing the EPS forming strain within a PBR supplemented by tuned LED PAR (Photosynthetically Active Radiation 400-700 nm) lighting to provide continuous illumination over anywhere between 1 and 24 hours of the algae each day; (c) after peak exponential phase of growth moving a portion such as approximately 50% of the yield to a static illuminated tank system with gentle aeration (ambient air without addition of $CO_2$) to enhance the EPS formation over 3-4 days; (d) dewatering the algal paste for extraction of the biopolymer or for other uses described above or for energy production via ethanol fermentation or other processes (e.g. anaerobic digestion or biomass gasification).

Examples of the gelatinous coated strains of micro-alga suitable for use in the invention may reside within the Chlorophyta and selected from the family Dictyosphaeriaceae.

Adapted Strains of Algae

The micro-algal strain used for EPS production is maintained in heterogeneous supplies of industrial process water in standard flask cultures and supplied PAR lighting via low energy LED rigs with tuned light patterns. The light can be supplied internally within the PBR or externally. The cultures are sub-cultured each month to select for cells adapted to the waste water constituents and LED lighting. This phenotypic selection process includes an assessment step to check for the EPS production at each sub-culturing. Mother cultures are maintained under these growth conditions to continue the adaptation process.

Growing Algae in Photobioreactors ("PBRs")

A great deal of work has been done to develop small scale PBRs for the production of micro-algae (g). Commercial-scale PBRs (>100,000 L) should have large volume capacities and have a small footprint in terms of space occupied. In addition, they should have transparent surfaces, high mass transfer rates and should be able to produce large biomass yields. Furthermore, any design of PBR should take into account the unique needs of individual strains of micro-algae and be low maintenance and robust.

It has been suggested that the PBRs can also act as culture vessels for the outdoor pond growth systems. Given that outdoor PBRs are usually naturally illuminated using sunlight, biomass productivity would depend on the prevailing year-round environmental conditions in that locality. There are seasonal variations in temperatures and sunlight throughout the year in most regions which have been tested (often desert environments) hence it is difficult to carry out outdoor mass cultivation of algae all year round in such regions. There are a number of designs for PBRs in the public domain, being sold commercially and designs in academic articles but no definitive 'best practice' standard model exists.

In a first set of embodiments any PBR apparatus (air lift tubular design or flat tank) which has device to drain or harvest the cells on a daily basis can be illuminated for part of or a continuous 24 hour day with PAR wavelengths of LED lighting (internally or externally) can be employed. The algae growth is monitored by an attached process control device to measure OD 680 nm which is correlated with cell numbers by prior reckoning and allows the determination of peak exponential growth from PBR commissioning. The system encompasses, but is not limited to, inclusion of highly tuned LED light sources which are designed to provide 360 degree angle illumination from the centre of a bioreactor to maximise the growth of different algae strains (growing around the light source).

On reaching peak exponential growth 50% of the cells are harvested daily to a separate batch holding tank which has aeration (ambient air mix) attached and LED lighting 24/7. The algal strains are held under prescribed conditions for 3-4 days and samples from the tank monitored visually under a microscope daily for EPS production. These cells are finally extracted via dewatering for either carbohydrate extraction or for the uses described earlier.

Light Sources

Algal culture systems can be illuminated by artificial light, solar light or both. One of the most important factors to control high biomass micro-algal production in the closed PBR is the light irradiance and the quality of light spectrum delivered. If the PBR is positioned outdoors, it can be limited to the high light levels seen in the daytime and during the summer months but this will vary geographically. The levels of Ultra-Violet light ("UV") in natural sunlight can also cause photo-inhibition of algae at certain times of the day and hence lacks the potential control of the PBR grown using artificial light.

One major light source which can supply specific light wavelengths is the range of Light-Emitting Diodes ("LED") which are now being developed by several major light manufacturers. LEDs have the ability to save energy and have a very long life-expectancy. Their electrical efficiency helps to minimise heat generation. This high efficiency and sharp spectrum have eliminated the need for a cooling system and filter and therefore reduced energy input requirements significantly. These factors open up the potential to optimise light delivery for specific strains of micro-algae (h).

It is known which parts of the Photosynthetically Active Radiation (PAR) spectrum (400-700 nm which covers red and blue ends of the spectrum) could help maximise efficient photosynthesis of algae in general but few data exist (in the public domain) on specific interactions of such light irradiance on the growth and physiological status of biofuel precursors (lipids/carbohydrates) for different algae strains grown under artificial light in PBRs. The applicants have discovered the precise Red/blue LED requirements and irradiance levels delivered for a range of micro-algae and for the dual stage process of EPS production here.

'Sustainable' Energy Inputs for PBR Systems

The potential use of 'waste' streams, where scrubbed flue gases provide $CO_2$ with amended process water used as a nutrient medium for algal growth, has been debated at great length in the literature. There are a few significant, or successful, demonstration projects which have been established to date. It has been estimated that using hybrid systems, algae may be used to recycle 20% of industrial power generation $CO_2$ emissions. If novel and cheap sources of capturing $CO_2$ can be developed this will reduce the cost and energy requirements of PBRs.

The process of growing algae in the industrial process water can reduce the nutrient levels to levels potentially required with evolving strict legislation targets in different parts of the world for discharging water into the environment and particular bodies of water.

The applicants have discovered the optimum nutrient levels required under controlled temperature and light irradiance levels for cost effective growth of the algae described in this document.

Algal Biomass and Biopolymers

Algal polysaccharides are currently used commercially (d). Soil algae are known to excrete a variety of extracellular polymeric substances (EPS) especially polysaccharides which may play an important role for their vital function (e). The exopolysaccharide (EPS) forming algal strain has the benefit of also being used in water to remediate by sequestering potentially toxic elements within the EPS formed at the batch stage and before. There is clear evidence that elements like Copper can be bound by these mucilaginous compounds (i). This has a clear value where water clean up for downstream discharge or use is the primary aim. In the carbohydrate analysis done on the EPS composition showed 94-95% neutral monosaccharides and about 5-6% uronic acid. The latter is particularly important for the binding of heavy metals.

It is known that soil algae enhance soil formation and water retention, stabilize soil, increase the availability of nutrients of plant growing nearby and reduce soil erosion. They have been introduced as soil conditioners in many countries and they have also been suggested for use as biofertilizers (j).

The decreasing supply of 'sweet' water will increase the need for use of recycled water and secondary treated water has been used for fresh market vegetables and fruit production in Israel using irrigation systems. However it does need the regulations in many countries to be amended for its widespread use even with SDI where the treated water does not reach the edible portions of the crop (above ground).

Traditional drip irrigation is found aboveground, but recently numerous companies manufacturing drip irrigation systems have invented and implemented subsurface drip irrigation (SDI) systems. The lines are buried below ground for a longer life. Subsurface irrigation allows the precise application of water, nutrients and other agro-chemicals directly to the root zone of plants. This allows the farmer to optimize the growing environment and leads to higher quality crop yields.

When properly managed SDI is one of the most efficient methods of irrigating plants with efficiencies >90%. The savings in applied water can be as much as 50% compared with other methods. The quantity of water available for irrigation is expected to decline in coming decades and water conservation more important. This is where SDI is crucial by extending the life of aquifers. Its use for biofuel crops has great potential and it has been shown in poor soils that the use of SDI can double the yields of sugar cane and its sugar content increased whilst conserving 70% of the water requirement (k).

The exopolysaccharide of an adapted strain of *Dictyosphaerium chlorelloides* ALG03 can also be used for the downstream production of bioethanol using the extracted carbohydrates. The remaining carbohydrates and proteins can be used for other by-products such as food additives and animal feed.

The invention will be further understood with reference to the following non-limiting examples.

EXAMPLES

Example 1

Algae belonging to the family of Pleurochloridaceae or cyanobacterial order Chroococcales in the genera *Synechocystis* and *Synechoccocus* were pre-incubated in nutrient amended water and continuous PAR lighting conditions (within the 400-700 nm wavelengths) for a period of 6 months and subcultured at regular intervals. The isolated cultures were sub-cultured further to bring them into exponential growth phase and used in a series of 50 L bioreactors. The starting cell density of the algal inoculum was $10^6$ cells per milliliter taken from the sub-cultured algae which was transferred to a 50 L bioreactor containing nutrient amended water and allowed to reach exponential growth phase in the presence of continuous PAR lighting conditions (wavelengths between 400-700 nm). The process was controlled for various parameters including; pH (maintained between 6-9); Temperature (maintained between 20-40° C.); aeration (0.02 to 1.0 v/v/m—Air volume per volume of liquid per minute); and/or $CO_2$, (0% at start up finishing at least 0.7% at first harvest but can reach 5% within the system overtime); $O_2$ maintained between 500-800 mV); maximum light irradiance at first cells in PBR (600 µmol $m^{-2}$ $s^{-1}$) aeration, $CO_2$ (starting at 0% added $CO_2$ and rising to 0.7% by harvest), cell density, temperature (27° C. average) and light delivery (24 hours a day). On reaching the near maximum exponential growth 500 g wet algae biomass product was removed from reactors. A solvent mix containing Methanol/Acetyl Chloride/Hexane was added producing methyl esters of the native lipid acids. The methyl esters were separated by chromatography using hexane and acetone solution and subsequently evaporated to obtain 1.6 g Eicosapentaenoic acid. Chromatography also provided pure samples of Myristic acid, Palmitic acid Behenic Acid, Lauric acid, Linoleic acid, alpha Linolenic acid and Stearic acid and the like.

Example 2

50.08 g of biomass was dried for 6 hrs at 105° C. After cooling down in an exicator the sample was placed for 1 hour in an oven at 105° C. and again weighed. In a Soxhlet extraction device the dry biomass was extracted in 260 ml of petrol ether for 8 hours in an extraction capsule. After evaporation of the solvent in a vacuum rotation evaporator the sample was further dried by passing a fine stream of Nitrogen over the sample and again weighed after cooling. To obtain the lipids the sample was dissolved in 50 ml of hexane and divided in half. Ten grams of activated charcoal was added to the first sample and the solution was filtered and again evaporated and streamed with Nitrogen and weighed. There was still some colour present therefore for the second sample 20 g of activated charcoal was used.

The samples were analysed using an Agilent Technologies 6890N and a column HP 88, cyanopropyl—Length: 100 m—diam: 0.25 mm, width of layer: 0.20 µm.

TABLE 1

The results of analyses of the percentages of 3 Fatty Acids linked by their metabolic pathway from 3 different batch PBR cycles

| Fatty Acid | Percentage of Fatty Acid ME in Total Lipid Pool of *Chlorogibba allorgei* | | |
|---|---|---|---|
| | Approaching end of Log Phase Growth | Partial Stress post log growth (Post-Harvest Day1) | Post Full Stress (Day 3 - stationary phase) |
| γ-Linolenic acid (GLA) | 18.0 | 11.0 | 0.7 |
| Arachidonic acid (ARA) | 2.4 | 3.7 | 0.0 |
| Eicosapentaenoic acid (EPA) | 20.0 | 23.5 | 27.0 |

The results clearly indicate the switch from GLA to EPA via ARA as the algal strain is growing and then induced to enter the stationary phase post stimulus as described above. This is evidence that the process described herein is directly managing the perceived metabolic pathways which allow interconversion between γ-Linolenic acid and Eicosapentaenoic acid via Arachidonic acid in freshwater microalgae (I).

Example 3

Figure 5B:
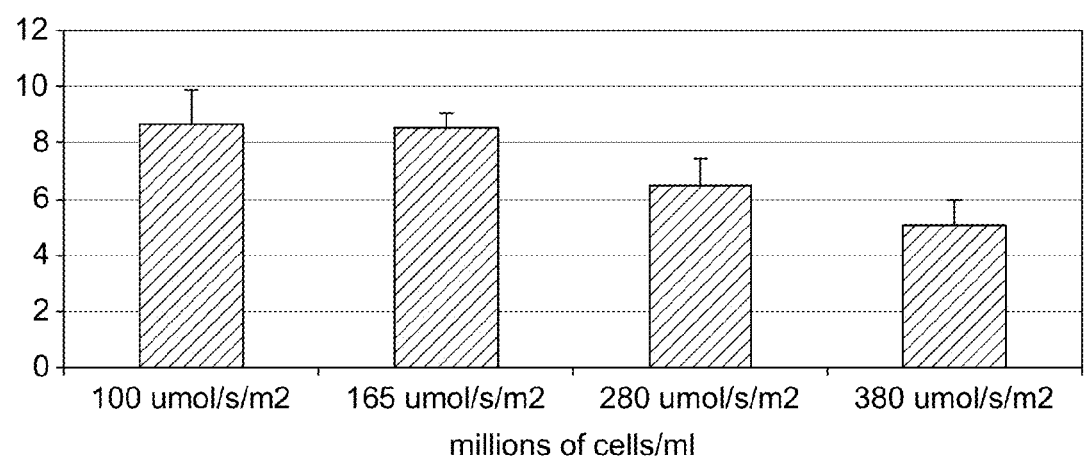

*Dictyosphaerium chlorelloides* (ALG03) was grown over 4 days in Bold Basal Medium. FIG. 5a shows that the alga needs relatively low levels of nutrients for optimal growth at 27° C. under optimal light irradiance. FIG. 5b shows that alga grows best in low light over 7 days in 25% BB medium at 27° C.

During a continuous production process, *Dictyosphaerium chlorelloides* (ALG03) were harvested daily. FIG. 7, with biomass shown as optical density (680 nm) readings in PBR, shows that daily harvesting at 50% rates enables regrowth of same biomass of *Dictyosphaerium chlorelloides* (ALG03) within 24 hours when topped up with new growth medium.

Physiologically adapted cells were grown for 6 months in waste water from municipal plant (Secondary treated) and re-cultivated each 4 weeks into new waste water. Non-adapted cells were cultivated in standard ZBB growth medium and re-cultivated every 4 weeks into new ZBB medium. Then both strains were grown for 9 days (until stationary phase) in new waste water. Results (FIG. 8) show a clear adaptation to the waste water environment and LED lighting by pre-adapted cells. FIG. 9 shows the doubling of EPS production following the 2 stage PBR process.

Subsequent steps of the method included purification, isolation of the EPS and hydrolysis of the sample using methanolic HCl followed by Trifluoroacetic acid.

The exopolysaccharides comprises 94-95% neutral monosaccharides with 5-6% uronic acid. Some neutral monosaccharides are partially methylated. The predominant sugars were:
  galactose (~20-21%)
  glucose (~20-21%)
  nonidentified hexose (~12-13%)
  rhamnose (~12%)
  nonidentified methylated hexose (~9-10%)
  nonidentified methylated hexose (~7-8%)
  mannose (~6-7%)
  xylose (~3-4%)
  arabinose (~1-2%)
  unknown monosaccharide (~up to 0.5%)
  unknown monosacharide (~0.5-1.0%)
  uronic acids (~5-6%).

The Molar ratio of sugars in dried gel and lyophilised samples of hydrolysed EPS are shown in Table 2.

TABLE 2

| | Molar ratio of sugars (%) | |
|---|---|---|
| | F1 | F2 |
| Fucose | 2.73 | 0.81 |
| Rhamnose | 10.20 | 15.54 |
| Arabinose | 5.34 | 8.28 |
| Galactose | 9.83 | 15.10 |
| Glucose | 65.31 | 51.12 |
| Mannose | 4.32 | 6.86 |
| Xylose | 2.27 | 2.29 |

Example 3

The results of using drip irrigation to grow leek in an infertile sandy soil in a greenhouse trial over a 12 week period can be seen in the image in FIG. 11. From left to right: Control no algae; mycorrhizal fungal symbiont (mix of *Glomus* spp.) used at planting; algae used weekly; algae and mycorrhizal fungal symbiont. Results clearly show a growth promoting effect of *Dictyosphaerium chlorelloides* ALG03 cells added twice weekly on growth and nutrition of a leek. A synergistic effect of algal cell use with an adapted mycorrhizal fungal symbionts mix was observed.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate.

Various publications are cited herein, the disclosures of which are incorporated by reference in their entireties.

REFERENCES a. Chisti Y—2007—Biodiesel from microalgae. Biotechnol. Adv. 25(3):294-306.
b. Olaizola M—2005 Microalgal removal of $CO_2$ from flue gases: Changes in medium pH and flue gas composition do not appear to affect the photochemical yield of microalgal cultures. The Korean Society for Biotechnology and Bioengineering 8: 60-367.
c. Braun A R—1996 Reuse and Fixation of $CO_2$ in Chemistry, Algal Biomass and Fuel Substitutions in the Traffic Sector. Energy Conyers Manage., 37:1229-1234.
d. Bitton R & Bianco-Peled H—2008 Novel Biomimetic Adhesives Based on Algae Glue. Macromolecular Bioscience 8:393-400.
e. Otero A & Vincenzini M—2003 Extracellular polysaccharide synthesis by Nostoc strains as affected by N source and light intensity. J. Biotechnol. 102:143-152.
f. Gonzalez-Chavez C., D'haen J, Vangronsveld J. & Dodd J C—2002 Copper sorption and accumulation by the extraradical mycelium of different *Glomus* spp. of arbuscular mycorrhizal fungi isolated from the same polluted soil. Plant and Soil 240: 287-297.
g. Ugwu C U, Aoyagi H and Uchiyama H—2008 Photobioreactors for mass cultivation of algae. Bioresource Technology, 99, 4021-4028.
h. Choul-Gyun Lee—1999 Calculation of Light Penetration Depth in Photobioreactors Biotechnol. Bioprocess Eng., 4, 78-81.
i. Garcia-Meza, J V, Barrangue C & Admiraal W—2005 Biofilm formation by algae as a mechanism for surviving on mine tailings. Environ. Toxic. & Chemistry. 24:573-581.
j. Painter T J—1993 Carbohydrate polymers in desert reclamation—the potential of microalgal biofertilizers. Carbohydrate Polymers, 20, 77-86.
k. Netafim™ Website, Article, Sugar Cane.
(l) Khozin-Goldberg, I., Didi-Cohen, S., Cohen, Z., 2002. Biosynthesis of eicosapentaenoic acid (EPA) in the freshwater eustigmatophyte *Monodus subterraneus*. J. Phycol. 38, 745-756

The invention claimed is:

1. A process for the enhanced production of: (a) eicosapentaenoic acid in a microalgal strain selected from the family Pleurochloridaceae; or (b) exopolysaccharide in microalgae selected from the genus *Dictyosphaerium*, said process comprising the steps of:
   (i) culturing a said microalgal strain through a production phase;
   (ii) exposing the microalgal culture to a stimulus, wherein the stimulus comprises (a) a decrease in pH to a pH of no more than around pH 6, followed by an increase in pH to a pH of no less than around pH 7 and (b) an increase in light irradiance to at least 400 µmol/m²/sec.

2. The process of claim 1 wherein the stimulus comprises one or more of:
   (a) a decrease in pH from a pH of between around pH 7 and pH 9 to a pH of between around pH 5 and pH 6;
   (b) an increase in LED-delivered irradiance from between around 50-200 µmol/m²/sec to between around 400-2000 µmol/m²/sec.

3. The process of claim 1 wherein one or more of the following applies to the production phase:
   (a) the production phase corresponds to the exponential phase of growth;
   (b) the production phase involves growth of the microalgal strain under conditions that permit exponential growth;
   (c) the production phase involves growth of the microalgal strain in a photobioreactor;
   (d) the production phase involves growth of microalgae under LEDs emitting 2 peaks of red and blue light within the Photosynthetically Active Radiation (PAR) spectrum 400-700 nm.

4. The process of claim 1 wherein:
   (a) the cultures are not exposed to natural sunlight,
   (b) the microalgal culture is exposed to the stimulus at the peak of exponential phase growth and/or at the onset of the stationary phase of growth,
   (c) the stimulus additionally comprises addition of a carbon source; or
   (d) the decrease in pH is initiated by the addition of $CO_2$.

5. The process of claim 1 wherein the pH is lowered to a pH of between around pH 5 and pH 6 for a period of between around 30 minutes and around 2 hours, and said period precedes the increase in light irradiance.

6. The process of claim 5 wherein after the pH decrease, the pH is increased to a pH of between around pH 7 and pH 9.

7. The process of claim 1, wherein: following exposure of the microalgae to the stimulus, the microalgae are cultured for a further period of around 48 hours prior to the harvesting of the metabolite.

8. The process of claim 1 wherein the microalgae in the family Pleurochloridaceae are selected from:
   (a) the species: *Trachydiscus* sp. and *Chlorogibba* sp.; and
   (b) a strain of *Chlorogibba allorgei* deposited with the Culture Collection of Algae and Protozoa under the accession number CCAP 817/1, or a mutant strain derived therefrom;
   and the microalgae in the genus *Dictyosphaerium* are selected from:
   (a) the species *Dictyosphaerium chlorelloides*; and
   (b) a strain of *Dictyosphaerium chlorelloides* deposited with the Culture Collection of Algae and Protozoa under the accession number CCAP 222/98.

* * * * *